(12) United States Patent
Barrick

(10) Patent No.: US 6,240,923 B1
(45) Date of Patent: Jun. 5, 2001

(54) PELVIS IMMOBILIZER

(76) Inventor: E. Frederick Barrick, 8904 Gallant Green Dr., McLean, VA (US) 22101-1515

( * ) Notice: Subject to any disclaimer, the term of this patent is extended or adjusted under 35 U.S.C. 154(b) by 0 days.

(21) Appl. No.: 09/439,290

(22) Filed: Nov. 15, 1999

(51) Int. Cl.⁷ ................................................. A61B 19/00
(52) U.S. Cl. ............................. 128/869; 128/876; 602/19
(58) Field of Search ................................... 128/845, 846, 128/869, 876; 602/19; 2/311, 312, 321

(56) References Cited

U.S. PATENT DOCUMENTS

| | | |
|---|---|---|
| Re. 34,883 | 3/1995 | Grim . |
| 3,441,027 | * 4/1969 | Lehman .................................. 602/19 |
| 3,509,875 | * 5/1970 | Richter .................................... 602/19 |
| 4,099,524 | 7/1978 | Cueman et al. . |
| 4,175,553 | * 11/1979 | Rosenberg ............................... 602/19 |
| 4,211,218 | * 7/1980 | Kendrick ................................. 602/19 |
| 4,481,941 | * 11/1984 | Rolfes ..................................... 602/19 |
| 4,545,370 | 10/1985 | Welsh . |
| 4,580,555 | 4/1986 | Coppess . |
| 4,665,908 | 5/1987 | Calkin . |
| 4,993,409 | 2/1991 | Grim . |
| 5,178,163 | 1/1993 | Yewer, Jr. . |
| 5,267,947 | 12/1993 | James et al. . |
| 5,407,422 | 4/1995 | Mattijs et al. . |
| 5,433,697 | 7/1995 | Cox . |
| 5,484,395 | 1/1966 | DeRoche . |
| 5,547,462 | 8/1996 | Lanigan et al. . |
| 5,632,723 | 5/1997 | Grim . |
| 5,776,087 | 7/1998 | Nelson et al. . |
| 5,833,638 | 11/1998 | Nelson . |

OTHER PUBLICATIONS

Johnson & Johnson Orthopaedics, 1998, pp. 40 and 41.
Samuel G. Agnew, MD, "Hemodynamically Unstable Pelvic Fractures", Orthopedic Traumatology: Complex Fractures and Associated Injuries, vol. 25, No. 4, Oct. 1994, pp. 715–721.

Alexander G. Ghanayem, Md, et al. "Emergent Treatment of Pelvic Fractures Comparisonof Methods for Stabilization", Clinical Orthopaedics and Related Research, No. 318, 1995, pp. 75–80.

Gary S. Gruen, Md, "The Acute Management of Hemodynamically Unstable Multiple Trauma Patients with Pelvic Ring Fractures", The Journal of Trauma, vol. 36. No. 5, 1994, pp. 706–713.

Carl L. Holm, Md. "Treatment of Pelvic Fractures and Dislocations Skeletal Traction and the Dual Pelvic Traction Sling", Clinical Orthopaedics and Related Research, No. 97, Nov. –Dec. 1973, pp. 97–107.

* cited by examiner

Primary Examiner—Michael A. Brown
(74) Attorney, Agent, or Firm—Hoffman, Wasson & Gitler

(57) ABSTRACT

Disruption of the pelvic ring due to high energy trauma can cause severe bleeding from severed blood vessels, torn ligaments and fractured bone. Active intervention with compression of the injured pelvic bones can reduce the bleeding by a tamponade effect and by stabilizing the tissues. The pelvic fracture immobilizer has a wide band of firm material such as canvas and a plurality of straps, each having a ratcheting buckle. The pelvic fracture immobilizer provides for temporary compression and stabilization of a pelvic ring disruption without the need for the operative insertion of pins into or against the bones. Any trained medical personnel, including a nurse or technician, can use the immobilizer without harm, even in the prehospital setting. A surgeon is not necessarily required for its application. It is much less expensive than an external fixator. It is disposable. Its use does not interfere with subsequent internal fixation surgery. Being easy to use and inexpensive, it is much more likely to be used and thus provide benefit to a far greater number of patients than the external fixator has to date.

7 Claims, 4 Drawing Sheets

PELVIS IMMOBILIZER

BACKGROUND OF THE INVENTION

Disruption of the pelvic ring due to high energy trauma can cause severe bleeding from severed blood vessels, torn ligaments and fractured bone. Active intervention with compression of the injured pelvic bones can reduce the bleeding by a tamponade effect and by stabilizing the tissues. Current methods to intervene use some type of external fixation device applied to the pelvis. One such method is the insertion of two or three threaded metal pins into each iliac crest and the attachment of a frame of rods and connectors to hold the two innominate bones together.

Another method is the use of a large C-shaped clamp placed around the pelvis with one or more pins placed through the skin against the lateral aspect of each innominate bone and then tightened into place.

These devices were devised to firmly hold the disrupted parts of the pelvic ring together. They permit surgical access to the abdomen and perineum in the event it is needed. When initially devised these metallic external fixators were often used for many weeks for the definitive treatment of pelvic injuries.

There are a number of disadvantages to using these external fixators. There is a high complication rate, including infection, loosening, and injury to blood vessels. Some time is required to apply them, delaying the benefits of resuscitation. An orthopaedic surgeon is often needed to apply them, necessitating availability and experience. Two or more incisions are required to insert them. If infection around the pins occurs, it can impede, delay or prevent a more extensive definitive operation to stabilize the pelvic ring with internal fixation.

Also, an external fixator is more often now being used only for resuscitation and thus for a brief period of time, just long enough to stabilize the patient's condition. Then internal fixation is performed. In many cases many surgeons feel that an external fixator is no longer needed.

Earlier in this century, a pelvic sling was used to hold the disrupted pelvis together. It consisted of a canvas sling the height of which was approximately the vertical dimension of the pelvis. It would be placed under the pelvis, ropes attached to fasteners on each end, and traction applied to these ropes, sometimes crossing them over. The disadvantages of the pelvic sling have led to it rarely being used at this time. It was difficult to move the patient while in bed and not possible to move the patient out of bed without losing the effectiveness of the pelvic sling. The pelvic sling did not necessarily apply sufficient compression to effectively tamponade any bleeding or stabilize the injured pelvic bones.

There is a pelvic belt (U.S. Pat. No. 5,407,422) designed for chronic instability of the sacroiliac joint or pubic symphysis. It consists of a single narrow belt with a weak hook and loop type connector that would be unlikely to hold up under trauma situations with an expanding pelvic hematoma. The height of this belt is much less than the height of the pelvis and thus gives inadequate compression to the pelvic area. The buckle can be tightened only by pulling in one direction. Thus, forceful pulling would be likely to rotate the belt and make it difficult to apply the maximum force. Support belt (U.S. Pat. No. 5,178,163) is of similar construction. Kinetic back support belt (U.S. Pat. No. 4,545,370) is also of similar construction. It has a buckle that cannot be dynamically tightened.

Other back braces are designed for support of the lumbar region, rather than the pelvis. They are contoured to fit the natural lumbar lordosis. Most are elastic in the direction of support to provide comfort and compression, but not to resist expansion. None of the braces have a ratcheting buckle or connector that can easily and rapidly be tightened. None has a buckle that is tightened by pulling on both sides so that the brace will not rotate.

For example, a back brace (U.S. Pat. No. 5,833,638) uses a relatively weak hook and loop type fastener alone and is shaped to be worn "above the iliac crests." The back brace in U.S. Pat. No. 5,776,087 is "curved to underlie the curve of the lower ribs of the body." It is constructed with stays that fit into pockets, an unnecessary and uncomfortable feature if immobilizing the pelvis. It has the feature of straps that go over the shoulders, which indicates that the brace fits loosely. A fireman's back brace (U.S. Pat. No. 5,484,395) is a "lumbar spinal support" with an elastic tensioning strap that would stretch when an expanding force is applied. A further back brace (U.S. Pat. No. 5,547,462) consists of a single narrow belt with front and back panels. The panels give insufficient support to the sides of the pelvis. It applies pressure to the back rather than posterior aspect of the pelvis and the front panel rests against the "stomach" rather than the anterior aspect of the pelvis. A conformable back brace with an abdominal support (U.S. Pat. No. 5,433,697) has abdominal and lumbar support members or panels connected with narrow straps to each side. The brace conforms by placing straps through slats in these panels. The back support disclosed in U.S. Pat. No. 4,993,409 and the simplified orthopaedic back brace in U.S. RE 34,883 consists of an elastic material with an air bladder. These are unnecessary components. The connectors are the hook and loop type. It is designed to support the lumbar region. A contour lumbar support disclosed in U.S. Pat. No. 5,267,947 is made to fit the lumbar spine and to purposely not give lateral compression. Its buckle is a standard type that cannot be dynamically adjusted. The sacro-lumbar support belt is contoured for the lower back, and has a weak hook and loop connector with unnecessary stay pockets. This configuration would be uncomfortable with the patient lying supine. It is designed to lie against the patient's back.

There are a group of devices that are used for temporary splinting of the pelvis and spine. All use a firm support to immobilize the spine but they do not allow compression of the pelvic region. Portable pelvic and leg splints (U.S. Pat. No. 4,580,555) have an extension to splint the legs. They use buckles that pull from one direction that could tend to rotate the splint. A spinal restraint device (U.S. Pat. No. 4,211,218) extends to the head and neck and has straps that go between the legs. It has buckles that are tightened in a unilateral direction. It is open anteriorly that would permit swelling in the pelvic region to protrude. Extrication and spinal restraint devices (U.S. Pat. No. 4,665,908) do have buckles that do not rotate the device, but they have especially rigid back boards. They extend to the head and neck and between the legs also.

In fact, there are no previous braces, immobilizers or the like, that are designed to care for pelvic fractures.

SUMMARY OF THE INVENTION

The pelvic fracture immobilizer includes a wide band of firm material such as canvas and a plurality of straps, each having a dynamic ratcheting buckle. The band material can be elastic in the vertical plane but not in the horizontal plane. The elasticity in the vertical plane permits the immobilizer to contour to the shape of the pelvis and thus reduce the pressure on the bony prominences of the ilium and greater trochanter of the femur. The band comes in various sizes, the ideal length for each patient being the circumference of the pelvis in the injured state. In the preferred embodiment, the band becomes narrower at each end but the portion of the band that passes around the back and sides of the pelvis are of uniform height. This height is approximately the vertical dimension of the pelvis. The band is inelastic in its horizontal orientation so that if there is swelling it does not give and prevents further swelling. It is elastic in its vertical direction so that it conforms to the naturally irregular shape of the pelvis. If desired, there is a hook and loop, or other type fastener, at the ends where they come together so that the band can temporarily be held in place.

There are a plurality of straps (three are preferred) each having a length greater than the length of the band. The straps are approximately parallel and are securely attached to the band for most of their length but not attached at the ends where the band begins to narrow. There is a dynamic buckle for each strap. Each dynamic buckle has two parts that connect by a snapping device. The straps are tightened by pulling through a looping attachment to each part. The straps are pulled apart, thus creating tension. The dynamic buckle is radiolucent so that it will not interfere with obtaining x-rays of the pelvis that are essential in the care of the patient. The dynamic buckles can be dynamically tightened. Dynamic tightening includes pulling from two sides to keep the band centered. If some slack develops, further tension can easily be applied without having to detach the connecting mechanism of the buckles.

The band is placed around the pelvis so that the ends come together on the ventral or anterior aspect of the patient. The straps are placed into the dynamic buckles. The middle strap is first ratcheted tightly to compress the sides of the pelvis together. The other two straps are tightened across the anterior aspect of the pelvis in turn to secure the band, keeping it from slipping and provide further compression. Compression of the pelvis is facilitated by the application of manual pressure to each side of the pelvic ring by an assistant. Each strap can be tightened further until sufficient stability is attained. This action of tightening the band around the pelvis acts like an external fixator to immobilize the pelvis and reduce internal bleeding. Access to the abdomen and perineum can be facilitated by undoing the buckle for the upper or lower strap. Thus a plurality of straps is essential to the function of the pelvic fracture immobilizer. The multiplicity of straps also permits pressure to be applied more evenly over the irregular shape of the pelvis.

The band is inelastic in the direction of compression so that once it is in place swelling from an expanding hematoma cannot stretch the band and loosen compression. It is elastic in the vertical direction so that it will conform to the shape of the pelvis. Thus, there will be less pressure on the bony prominences about the pelvis.

Another version of the invention has the tapered ends. On one side the two outer straps cross over as described above. A single center band is attached to the opposite side. When the band is placed around the patient's pelvis, this single center band passes through a cutout in the first side attached to a center buckle placed at some distance from the end. The two crossover straps attach to buckles placed at a distance from the edge of the opposite side of the band.

Another version has two buckles at the outside edges of the band on one side. The ends of the band are squared. The two outer straps do not cross over. On the other side of the band there is one buckle in the center placed at some distance from the edge. There is a cutout in this side to accommodate the single centered strap that comes around to attach to this single buckle. The end of the band is tapered on the side of the free end of the single strap.

The pelvic fracture immobilizer provides for temporary compression and stabilization of a pelvic ring disruption without the need for the operative insertion of pins into or against the bones. Any trained medical personnel, including a nurse or technician, can use the immobilizer without harm, even in the prehospital setting. A surgeon is not necessarily required for its application. It is much less expensive than an external fixator. It is disposable. Its use does not interfere with subsequent internal fixation surgery. Being easy to use and inexpensive, it is much more likely to be used and thus provide benefit to a far greater number of patients than the external fixator has to date.

DETAILED DESCRIPTION OF THE INVENTION

Figure 1:
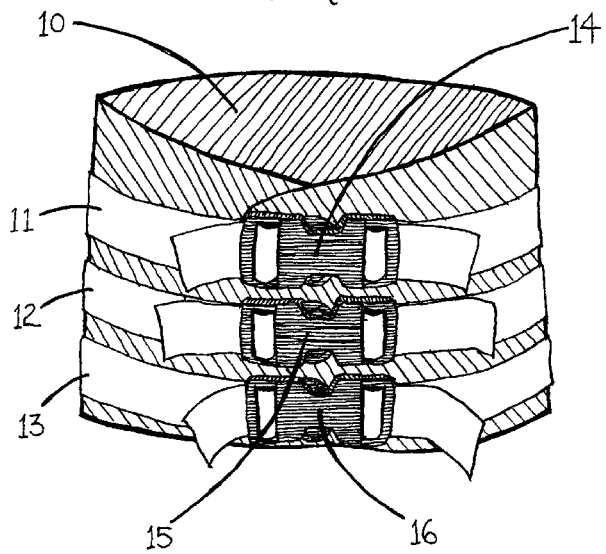
FIG. 1 shows an illustration of the pelvic fracture immobilizer from the anterior aspect.
Figure 2:
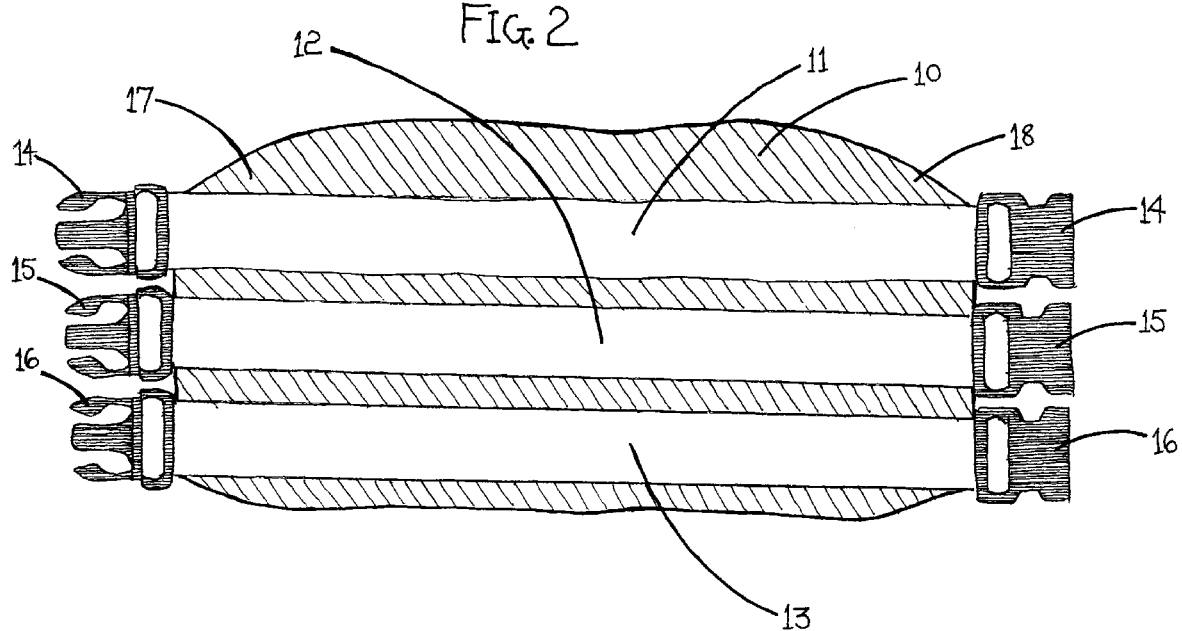
FIG. 2 is an illustration of the pelvic fracture immobilizer seen from the posterior aspect.
Figure 3:
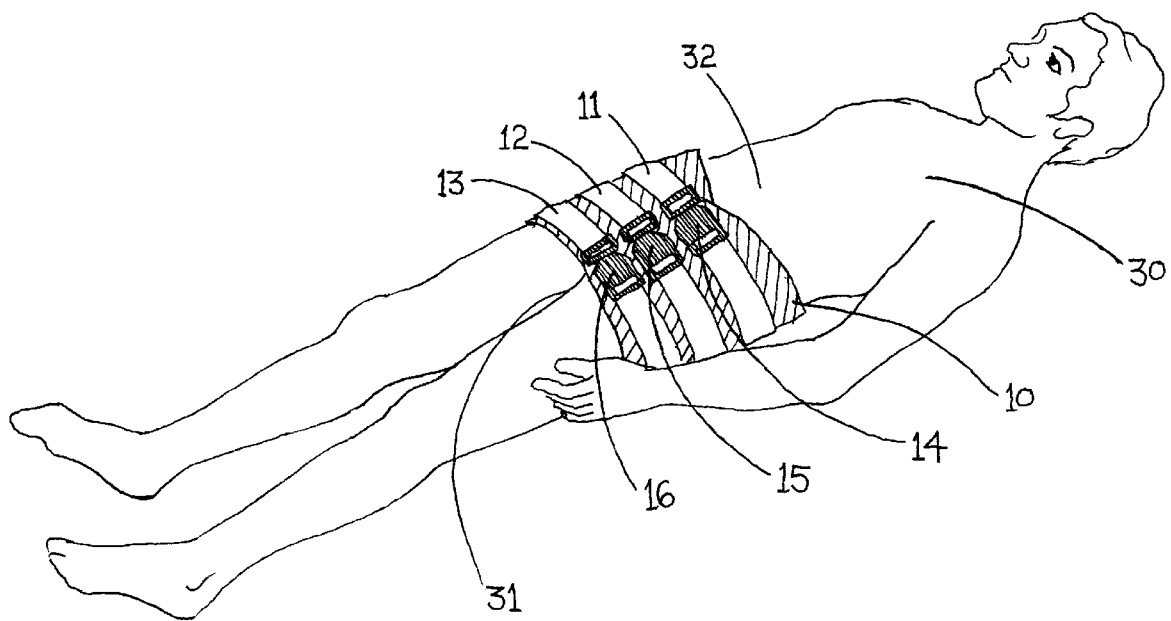
FIG. 3 is an illustration of the pelvic fracture immobilizer in place on a patient.

A pelvic fracture immobilizer 10 is made of inelastic strong fabric tapered at each end 17 and 18, as shown in FIGS. 1 and 2. A plurality of straps 11, 12 and 13 are attached to the pelvic fracture immobilizer 10 throughout most of the length L but leaving the ends free for attachment to the buckles 14, 15 and 16. The buckles 14, 15 and 16 have a friction device so that straps 11, 12 and 13, can be tightened firmly without slippage. One tapered end 17 fits under the other tapered end 18 when applied, as shown in FIG. 3. A first strap 12 is placed in a buckle 15 and cinched together to provide compression around the pelvis of a patient 30. A second strap 11 is placed in a second buckle 14 and a third strap 13 is placed in a third buckle 16. The second and third straps, 13 and 14, are tightened in turn.

FIG. 3 shows the pelvic fracture immobilizer 10 in place on a patient 30. Once the pelvic fracture immobilizer 10 is applied with compression by the tightening straps, 11, 12 and 13, the patient 30 can be turned in bed. Access to the abdomen 32 and the perineum 31 is possible if needed by unfastening the top or bottom buckles, 14 or 16, respectively.

Figure 4:
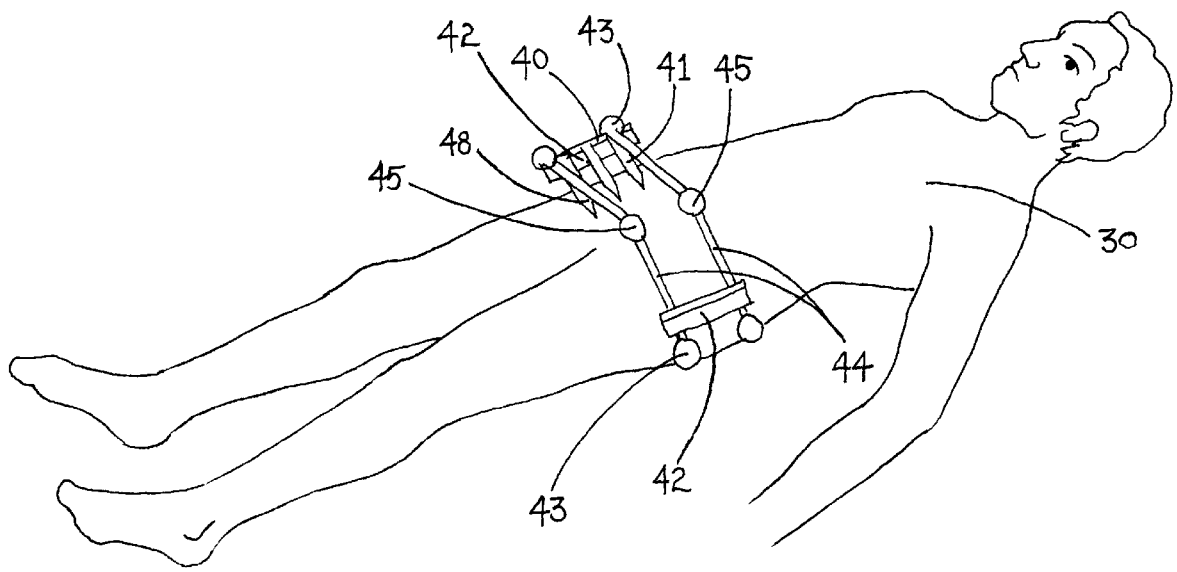
FIG. 4 is an illustration of a prior art external fixator in place on a patient.

FIG. 4 shows a prior art external fixator 40 in place on a patient 30. Six metal fixation pins 41 are placed into each side of the pelvis through incisions 48. Pin clamps 42 are attached to each set of three fixation pins 41. Connecting bars 44 are attached to the pin clamps 42 and are connected together with clamps 45 to secure and stabilize the pelvis.

Figure 5:
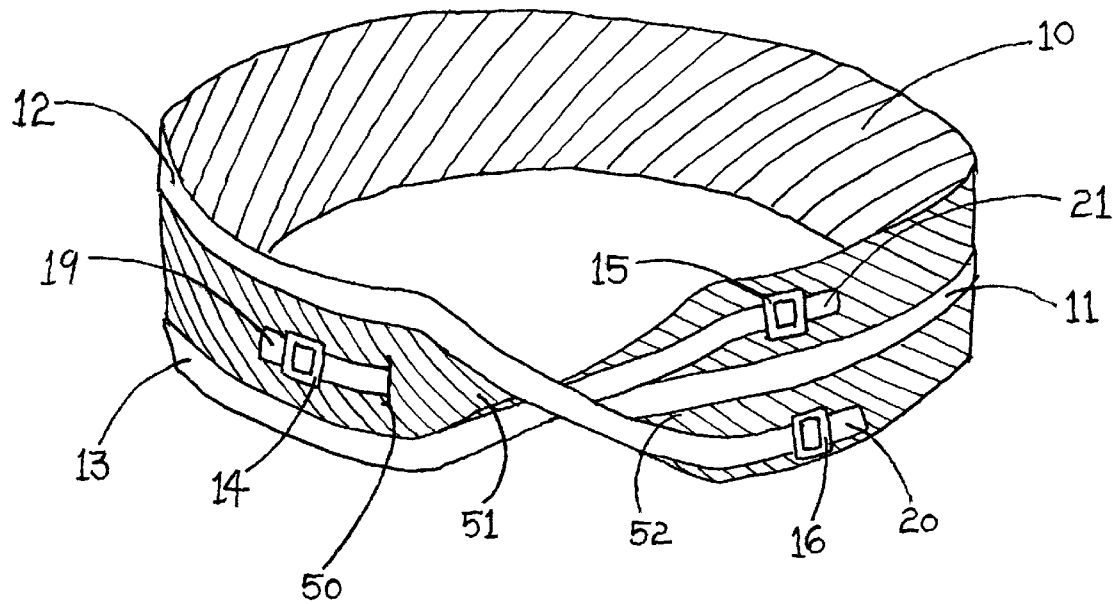
FIG. 5 is an illustration of an alternate embodiment of the pelvic fracture immobilizer as seen from the front.
Figure 6:
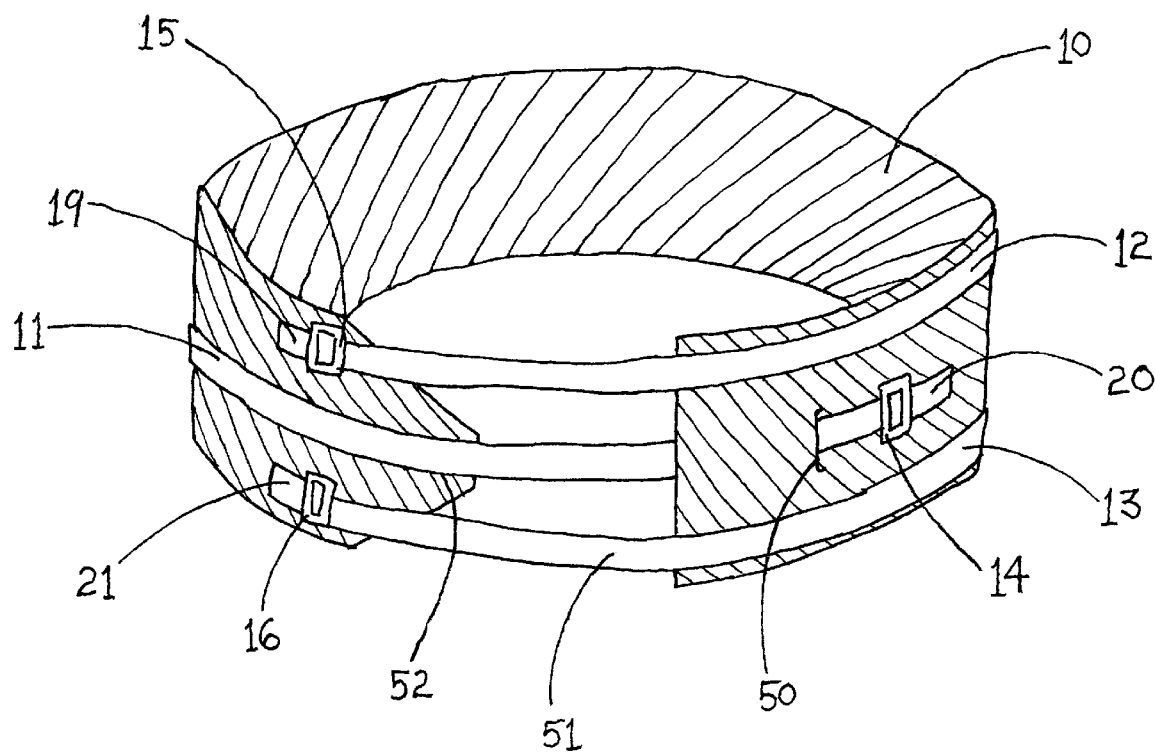
FIG. 6 is an illustration of an alternate embodiment of the pelvic fracture immobilizer viewed from the front.

Alternate embodiments of the pelvic fracture immobilizer 10 are shown in FIGS. 5 and 6. These straps, 11, 12 and 13, are attached to the pelvic fracture immobilizer 10 throughout most of the length but leaving the tails, 19, 20 and 21, of the straps, respectively, free for attachment to the buckles, 14, 15 and 16. The buckles, 14, 15 and 16, have a ratcheting device so that the straps, 11, 12 and 13, can be tightened firmly without slippage. Each pelvic fracture immobilizer 10 has a cutout 50 to permit a strap tail 21 to pass to another end 51 and thus permit the end 52 to pass under the other end 51 without folding into an uncomfortable position. The pelvic fracture immobilizer 10 is then cinched into place as noted above to provide compression around the pelvis.

The band 100 of the immobilizers of the invention is inelastic in the direction of compression (X axis) so that once it is in place, swelling from around the pelvis area cannot stretch the band 100 and loosen compression. The band 100 is elastic in the vertical direction (Y axis) so that it conforms to the natural irregular shape of a pelvis. The vertical length of the band 100 covers the entire length of the pelvis.

The dynamic buckles, 14, 15 and 16, are designed to allow for secure tightening without movement of band 100.

Further, means for initial fastening of the band 100 on the pelvis, such as hook and loop type fasteners, are used to hold the band 100 in place until the dynamic buckles, 14, 15 and 16, are secured.

While the principles of the invention have been disclosed, those reasonably skilled in the art will realize many modifications of structure, arrangement, proportions, elements, materials and components used in the practice of the invention which are particularly adapted for specific environments without departing from these principles.

What is claimed is:

1. A pelvis immobilizer comprising:

a) a band for engaging an entire pelvis of a user;

b) a plurality of straps fixedly attached to the band along almost an entire length of the band, each strap having two free ends;

c) a dynamic buckle adjustably attached to both free ends of each of the straps for securely holding the band on the pelvis of the user, wherein the straps are adjusted to securely tighten the band without rotation.

2. A pelvis immobilizer comprising:

a) a band for engaging an entire pelvis of a user;

b) a plurality of straps fixedly attached to the band along almost an entire length of the band, each strap having two free ends;

c) a buckle adiustably attached to both free ends of each of the straps for securely holding the band on the pelvis of the user, wherein the band is inelastic in a horizontal length to securely immobilize the entire pelvis of the user and elastic in a vertical length to conform to a shape of the pelvis of the user.

3. The pelvis immobilizer of claim 1, wherein the plurality of straps are three straps in a parallel arrangement on the band.

4. The pelvis immobilizer of claim 1, wherein the plurality of straps are three belts with a first strap crossing a third strap and each strap having tail ends that pass through cutouts in the band, the tail ends having thereon a ratcheting buckle to prevent slippage of the straps and the band on the pelvis of the user.

5. The pelvis immobilizer of claim 1, wherein the plurality of straps are three straps that are parallel and have tail ends that pass through cutouts in the band, the tail ends having thereon a ratcheting buckle to prevent slippage of the straps and the band on the pelvis of the user.

6. The pelvis immobilizer of claim 1, wherein said buckles are radiolucent.

7. The pelvis immobilizer of claim 1, further comprising d) hook and loop type fasteners on an end of the band for initial fastening of the band onto the entire pelvis of the user.

* * * * *